United States Patent
Rudin

(10) Patent No.: US 9,607,367 B2
(45) Date of Patent: Mar. 28, 2017

(54) ADAPTIVE PATTERN GENERATION

(75) Inventor: John Christopher Rudin, Bristol (GB)

(73) Assignee: Hewlett-Packard Development Company, L.P., Houston, TX (US)

( * ) Notice: Subject to any disclaimer, the term of this patent is extended or adjusted under 35 U.S.C. 154(b) by 211 days.

(21) Appl. No.: 14/382,352

(22) PCT Filed: Apr. 20, 2012

(86) PCT No.: PCT/EP2012/057316
§ 371 (c)(1),
(2), (4) Date: Sep. 2, 2014

(87) PCT Pub. No.: WO2013/156086
PCT Pub. Date: Oct. 24, 2013

(65) Prior Publication Data
US 2015/0023584 A1    Jan. 22, 2015

(51) Int. Cl.
G06T 7/00      (2006.01)
G03F 7/20      (2006.01)
G01N 21/956    (2006.01)
G01N 21/3563   (2014.01)
G01N 21/88     (2006.01)
G01N 21/95     (2006.01)

(52) U.S. Cl.
CPC ......... *G06T 7/0004* (2013.01); *G01N 21/956* (2013.01); *G03F 7/704* (2013.01); *G03F 7/70483* (2013.01); *G01N 21/3563* (2013.01); *G01N 2021/8854* (2013.01); *G01N 2021/9513* (2013.01)

(58) Field of Classification Search
None
See application file for complete search history.

(56) References Cited

U.S. PATENT DOCUMENTS

| | | | | |
|---|---|---|---|---|
| 5,309,108 A | * | 5/1994 | Maeda | G06T 7/001 324/501 |
| 6,819,469 B1 | * | 11/2004 | Koba | G03F 7/70291 359/290 |
| 7,050,659 B1 | * | 5/2006 | Williams | G02F 1/3511 385/14 |
| 7,485,576 B2 | | 2/2009 | Suh et al. | |
| 2004/0245227 A1 | | 12/2004 | Grafton-Reed et al. | |
| 2005/0207638 A1 | | 9/2005 | Staveley | |
| 2008/0176398 A1 | | 7/2008 | Jain et al. | |
| 2009/0220866 A1 | | 9/2009 | Barrett et al. | |
| 2010/0018956 A1 | | 1/2010 | Watts et al. | |
| 2010/0143848 A1 | | 6/2010 | Jain et al. | |

(Continued)

OTHER PUBLICATIONS

International Search Report, Apr. 15, 2013, Hewlett-Packard Development Company, L.P. Patent Application No. PCT/EP2012/057316, European Patent Office.

(Continued)

*Primary Examiner* — Bernard Krasnic
(74) *Attorney, Agent, or Firm* — HP Inc. Patent Department

(57) ABSTRACT

Embodiments of the present invention provide systems and method for adaptively generating a pattern for fabricating semiconductor devices, the method comprising obtaining image data of a surface, and dynamically modifying a pattern to be applied to the surface based on the obtained image data.

10 Claims, 5 Drawing Sheets

(56) References Cited

U.S. PATENT DOCUMENTS

Figure 1:
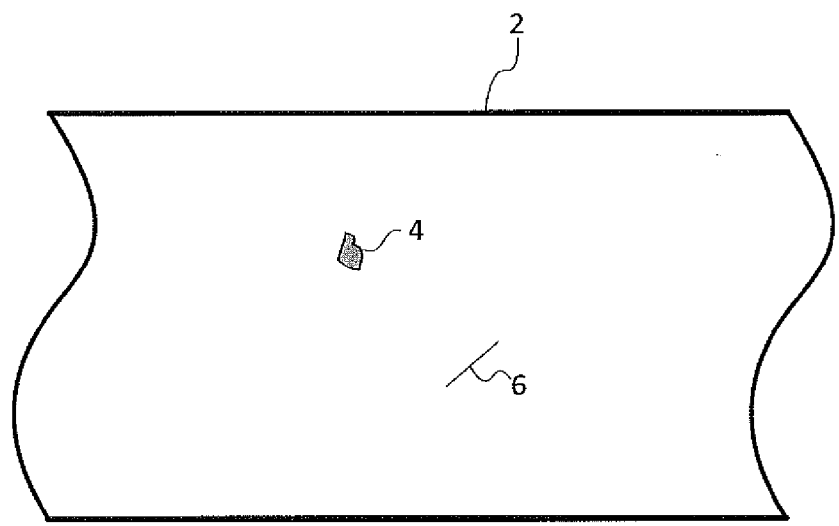

| | | | |
|---|---|---|---|
| 2012/0066651 A1* | 3/2012 | Pang | G03F 1/70 716/52 |
| 2012/0117520 A1* | 5/2012 | Kitamura | G03F 7/705 716/53 |
| 2014/0011123 A1* | 1/2014 | Okamura | G03F 1/24 430/5 |

OTHER PUBLICATIONS

Lin, Kevin L. et al., "Stretchable multilayer self-aligned interconnects fabricated using excimer laser photoablation and in situ masking." SPIE MOEMS-MEMS: Micromachining and Microfabrication Process Technology XIV, 2009, vol. 7204.

Tang, M. et al., "Maskless Multiple-Beam Laser Lithography for Large-Area Nanostructure/Microstructure Fabrication," Applied Optics, Dec. 2011, pp. 6536-6542, vol. 50.

* cited by examiner

ADAPTIVE PATTERN GENERATION

CROSS-REFERENCE TO RELATED APPLICATION

This application is a U.S. National Stage Application of and claims priority to International Patent Application No. PCT/EP2012/057316, filed on Apr. 20, 2012, and entitled "ADAPTIVE PATTERN GENERATION."

BACKGROUND

Plastic electronics, where functional devices are fabricated on, or are transferred to polymer substrates has been proposed as the future for large area systems such as displays, detector arrays and transducer arrays. Particularly when used to fabricate functional electronics for display applications, whether this is for Organic Light Emitting Diode (OLED), Liquid Crystal Displays (LCD), or Electronic Paper Displays (EPD), the number of layers to be fabricated or transferred to the polymer substrate is large, as is the number of functional processing steps that must be applied.

Typically, processes involving large numbers of layers to be fabricated over large areas with a large number of functional processing steps, such as when processing substrates for displays, a number of issues may be encountered.

These issues include ensuring good realignment of micron scale patterning, i.e. ensuring good alignment between different layers and features laid down in different processing steps. For example, when fabricating a simple three terminal TFT device, it is critical that the gate is correctly aligned to the source/drain contacts. For a polymer substrate dimensional stability is often poor, and measured in percent, as opposed to parts per million (ppm) for more traditional substrate materials such as glass or silicon, and therefore the processes used in the fabrication of devices on a polymer substrate typically relies on some level of self-alignment, serial processing (such as inkjet or aerosol deposition) or on slack design rules to ensure operation even with poor alignment.

The film surfaces used may include defects, even when high quality polymer substrates specifically produced for electronics use are used. Typically these defects include particulate, scratch or inclusion (bubble) types, and they can be a significant source of failure of devices and interconnects fabricated on the polymer substrate, leading to a very poor areal yield for the fabricated devices. This is critical when fabricating large area devices such as display and sensor arrays. These defects may be present in the original fabrication of the film, but can also be generated during the handling and processing, particularly during vacuum deposition of metals and polymers.

Furthermore, in order to identify and monitor yield problems during the fabrication process, high quality inspection is required to avoid processing substrates including defects, rendering any fabricated devices non-operative, through multiple, potentially expensive, further processing steps.

BRIEF INTRODUCTION OF THE DRAWINGS

Figure 2:
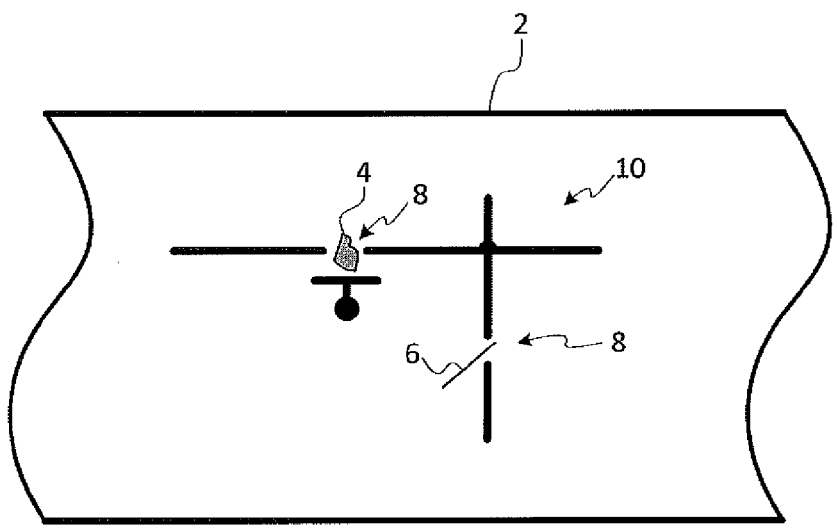
Figure 3:
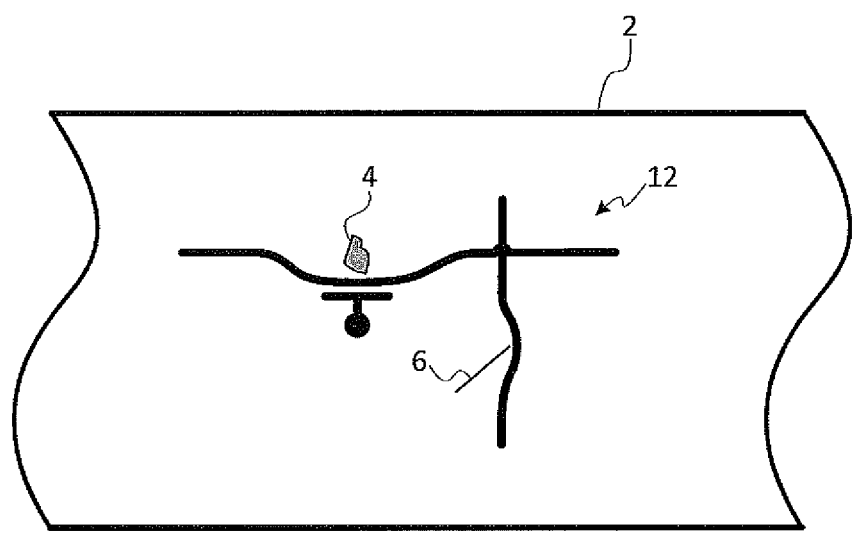
Figure 4:
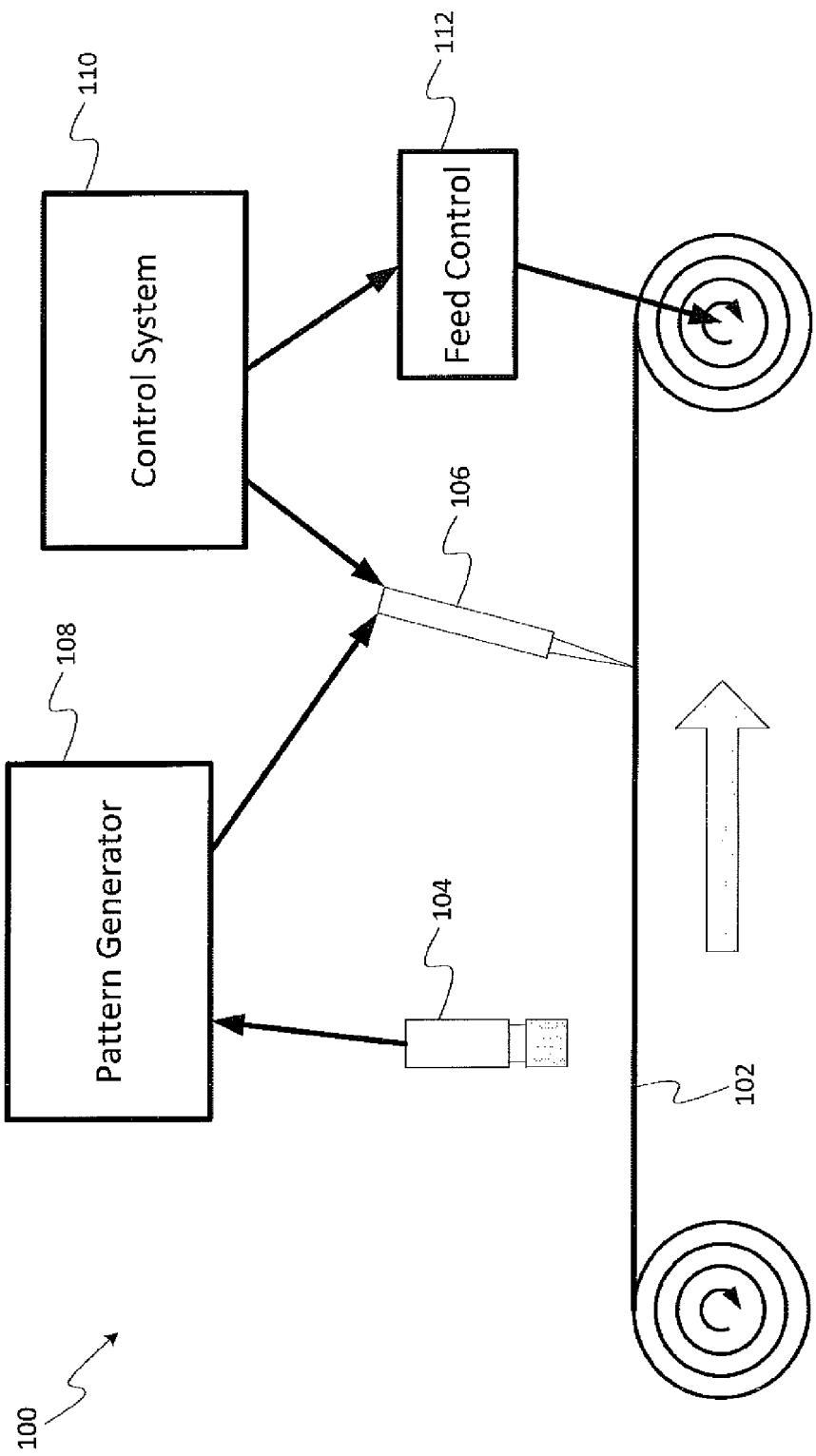
Figure 5:
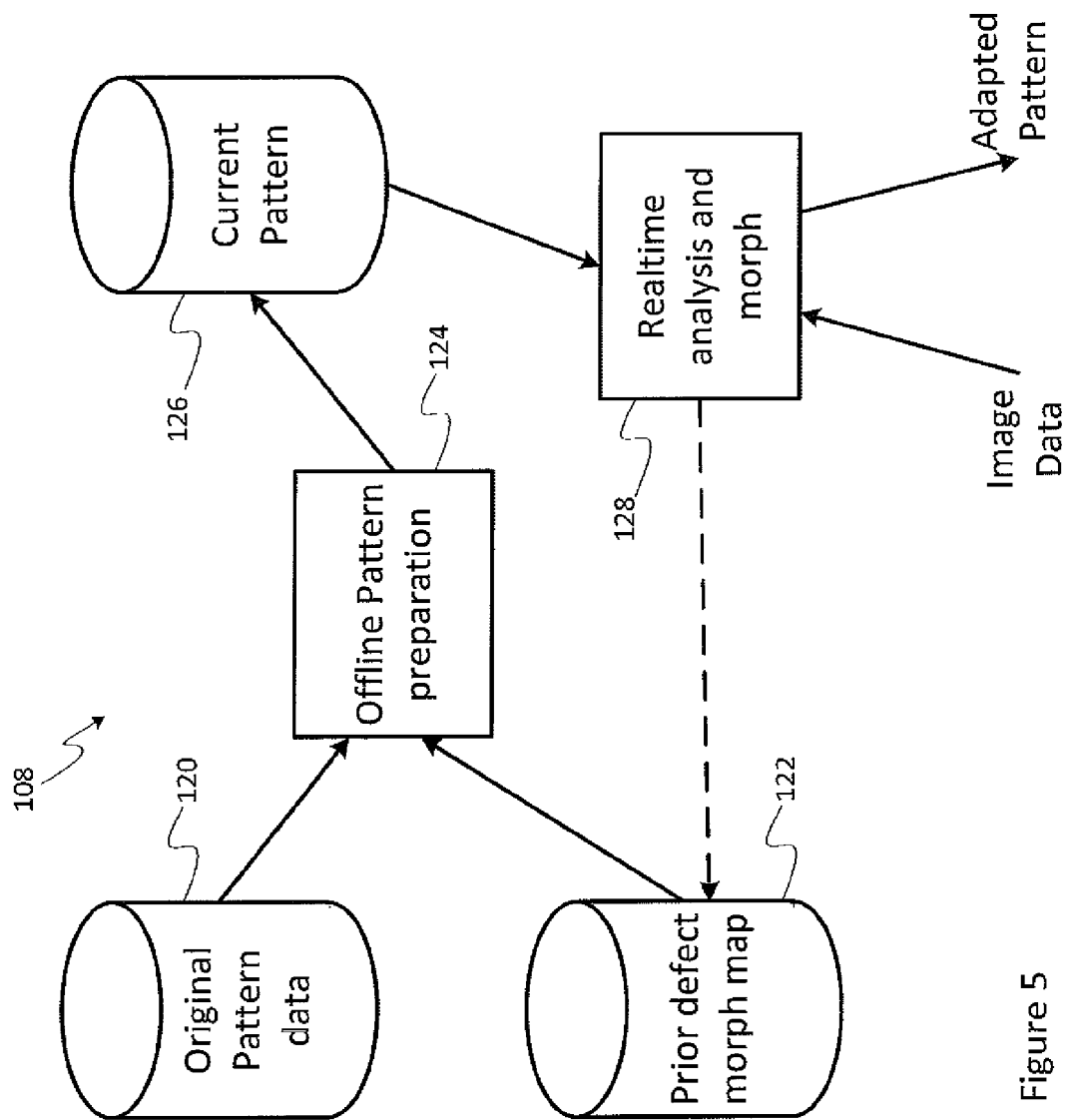
Figure 7:
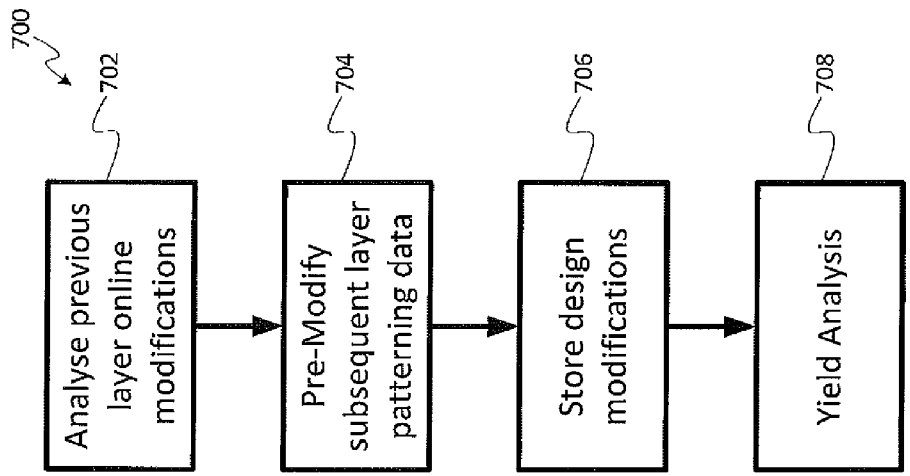
Figure 6:
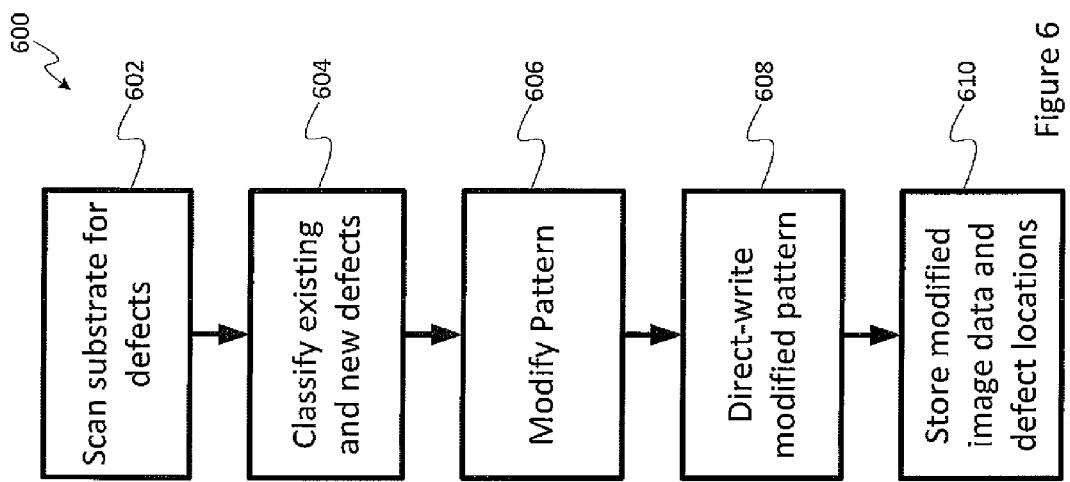

Embodiments of the present invention are further described hereinafter by way of example only with reference to the accompanying drawings, in which:

FIG. 1 illustrates a substrate including defects;
FIG. 2 illustrates the substrate of FIG. 1 after patterning with a fixed mask;
FIG. 3 illustrates the substrate of FIG. 1 after patterning with an adaptive patterning system;
FIG. 4 illustrates an apparatus for adaptively patterning a substrate;
FIG. 5 provides a more detailed illustration of the imaging system of FIG. 4;
FIG. 6 illustrates a method of adaptively patterning a substrate; and
FIG. 7 illustrates a method of analysing adaptive pattern modifications.

DETAILED DESCRIPTION OF AN EXAMPLE

FIG. 1 illustrates a substrate 2, such as a polymer substrate, including some defects within the main area of the substrate. These defects include a contamination (particulate) defect 4, and a scratch defect 6. Even when using high quality polymer substrates it is likely that some such defects will exist due to the large areas of substrate being processed.

FIG. 2 illustrates the result when a traditional fixed mask system is used to photo pattern features of a TFT array 10 onto the substrate 2. Due to the presence of the defects 4, 6 on the surface of the substrate, the pattern 10 is not able to correctly form across the whole area being patterned. In particular, pattern defects 8 occur leading to inoperative TFT devices and/or breaks in addressing lines of the array. Such defects 8 are likely to render the finished device inoperative, reducing the process yield and cost-effectiveness.

Embodiments of the invention provide an adaptive digital lithography system that is able to adaptively modify a pattern being patterned based on the presence of defects on the surface of the substrate. The adaptive lithography system morphs the pattern being applied to the substrate, optimally in real-time at production throughput rates, to avoid defects present in the substrate, without affecting the operation of the devices and/or the overall performance of the fabricated system (e.g. display or sensor array).

FIG. 3 illustrates an example of the adaptive patterning performed by the adaptive lithography system. By changing the pattern applied to the substrate 2, the patterned features 12 are morphed to avoid the particulate defect 4 and the scratch 6. Thus, in contrast to the example shown in FIG. 2 of Fixed mask patterning, the fabricated devices and addressing lines on the substrate remain operative, increasing potential yields when using substrates with defects.

The adaptive patterning system may also pre-distort any subsequent patterning layers to be applied to the substrate to compensate for any dimensional changes and a priori morphing of the patterns, as well as morphing subsequent layers to compensate for defects which have been introduced by any intermediate processing steps.

FIG. 4 illustrates an example adaptive digital lithographic system 100. In the example shown in FIG. 4, the substrate 102 comprises a long polymer film that operates on a reel-to-reel principle. The substrate is fed through the system from a first reel to a second reel under control of a feed control module 112. The substrate may make multiple passes through the patterning system in order to pattern multiple layers of electronic devices and interconnects, as commonly encountered in complex electronics.

As the substrate passes through the patterning system 100, a imaging device such as camera 104 scans the surface of the substrate 102 and passes captured image data to pattern generator 108. The pattern generator 108 then processes the captured image data to identify and classify defects on the surface of the substrate 100. Based on the identified defects, the pattern generator morphs the pattern to be applied to the substrate. The pattern generator 108 may be provided with one or more predefined rules to control how the pattern may be morphed or modified in the presence of defects on the surface. The pattern generator 108 then outputs the modified, or morphed, pattern to a high speed imaging system 106 which transfers the modified pattern to the substrate.

A control system 110 is coupled to the high speed imaging system 106 and to a feed control module 112. The feed control module 112 operates to control the movement of the substrate 102 through the adaptive digital lithographic system 100 under control of the control system 110. This positional information is also supplied to the high speed imaging system 106 in order to ensure that the modified pattern is applied to the correct position on the substrate.

The patterning system 100 is able to modify the pattern being applied to the substrate so as to avoid patterning critical features, such as TFTs, interconnects or vias of a semiconductor device array, on or near faults in the substrate, based on the image data of the substrate obtained by the imaging device 104. Furthermore, when the system 100 is used in a multi-step process, the image data can be used to modify further patterns to correctly align with a pattern that was previously applied to the substrate 102 in an earlier patterning step. In particular, the earlier pattern may itself have been morphed to avoid locating critical elements of the pattern over defects, or to correctly align with a yet earlier patterning step.

In some embodiments a multiple laser imaging, or pattern projection based on spatial light modulators system may be used as the high speed imaging system, 106. Such a system may be capable of imaging at more than 1 Gpixel/second. More preferably the imaging system may be capable of imaging at 5-7 Gpixels/second, at 1 μm addressability for a 3 μm feature size. This would allow a substrate to be processed at ~0.3 m2/minute, which on a 300 mm web is 1 m/minute linear feed, providing good production rates for the patterning system 100.

The imaging device 104 may comprise an imaging laser scanning at infra-red, or other wavelengths to feedback the position and type of defects in the polymer film and/or any prior coatings.

FIG. 5 provides a more detailed illustration of the pattern generator 108 of FIG. 4. The pattern generator 108 includes a realtime analysis and morph module 128 which receives the image data from imaging device 104 and analyses the received data to identify and classify defects on the surface of the substrate along with the location of classified defects. Details of the classified defects are provided to the prior defect morph map store 122 for use in offline pattern generation. A current image store 126 is coupled to the realtime analysis and morph module 128 and supplies pattern image data corresponding to a pattern to be applied to the substrate to the realtime analysis and morph module 128.

Using the pattern data supplied by the current image store 126, along with the location and type of defects determined from the received image data, the pattern data is modified to morph the pattern to avoid locating critical element of the pattern on or near defects. The modified pattern is then supplied by the realtime analysis and morph module 128 to the high speed imaging system 106. The modified pattern is further supplied to the defect morph map store 122 for use in the offline process.

The pattern generator module 108, further includes an offline pattern preparation module 124 configured to generate the pre-generate pattern image data to be stored in the current pattern store 126 in an offline process. The offline pattern preparation module 124 receives unmodified pattern data from original pattern data store 120, along with information relating to existing defects on the substrate and modifications made to a previous pattern layer from the prior defect morph map store 122.

The information received from the prior defect morph map store 122 is analyzed to determine the modifications made to the previous layer which must be taken into account to ensure accurate alignment of the subsequent layer pattern. Furthermore, the locations and types of previously identified defects on the substrate are noted. This information is then used to adapt the pattern data received from the original pattern data store 120 to ensure alignment between layers and to avoid patterning critical features of the new layer on or near previously identified defects. The adapted pattern data for the next layer is then stored in current pattern store 126 for use by the realtime analysis and morph module 128.

Thus, the pattern generator 108 operates in two stages: an offline pattern preparation stage in which an unmodified pattern is adapted to align with previous patterned layers and to take account of already identified defects based on information stored in the prior defect morph map store 122; and a realtime stage in which the pattern generated in the offline stage is further morphed based on newly captured image data to take account of any changes and/or alignment issues in a just-in-time fashion.

FIG. 6 illustrates an example method 600 corresponding to the above described realtime stage of pattern adaptation. In the method 600, the substrate is scanned for defects in step 602 using the imaging system 104. Defects are then classified according to type and whether the defects are pre-existing, i.e. have been previously identified, or are new in step 604. The pattern to be applied to the surface is then dynamically modified based on the classified defects in step 606. The modified pattern is then passed to the high speed imaging system 106 to be written to the surface of the substrate in step 608. Information relating to the classified defects, along with the modified pattern is then stored in the prior defect morph map store 122 in step 610 for use in the offline pattern generation process.

FIG. 7 illustrates an example method 700 corresponding to the offline processing of the pattern generation. In a first step 702 of the method 700, the pattern modifications relating to a previous layer are retrieved from the prior defect morph map store 122 and analyzed. The unmodified pattern data retrieved from the original pattern data store 120 is then pre-modified based on the analyzed data in step 704. The pre-modified pattern data is then stored in current pattern store 126 in step 706, ready for use in the realtime process 600. Subsequently, yield analysis can be performed based on the stored modified image data and defect locations in the prior defect morph map store 122 in step 708. In particular, any regions in which it has not been possible to adapt the patterns to avoid defects on the substrate, or to ensure alignment between layers can be identified, and further processing of any such areas of the substrate can be avoided to reduce waste.

As described above, the disclosed system and method provides a digital lithography system capable of adaptive pattern generation at production rates. Such a system may have significant advantages over fixed mask patterning systems. For example, the described system may be capable of accurate re-alignment of multiple layers of a fabrication process irregardless of any dimensional changes of the substrate during processing. Furthermore, as no masks are required as part of the fabrication process, costs relating to production of masks may be eliminated, and small production runs of customized products may become much more cost effective as the very high non-recurring expenses associated with mask and setup charges are no longer relevant.

Embodiments may further reduce overall production costs by allowing the use of lower quality, and therefore cheaper, substrates with higher areal defect rates without significantly affecting yields or the quality of the final product. Similarly, by avoiding defects present on the substrate, yields may be increased resulting in a lower per unit cost of the final product.

While the above discussion has concentrated on the fabrication of semiconductor device arrays, such as TFT array 10, it will be recognized that the disclosed techniques may be equally applicable to the fabrication of any electrical devices on the surface of the substrate including arrays of semiconductor devices, arrays of passive devices, or other devices fabricated on a film surface that would be sensitive to the presence of defects on the surface of the film, for example blocks of logic. Furthermore, as with more traditional fabrication methods, the disclosed method may be used to dynamically generate patterns for fabricating other types of device, for example photonic, MEMS, or fluidic devices to be formed on a substrate.

The described techniques may also be used to produce repair of rework patterns for substrates which have been processed using traditional fixed mask patterns, for example by detecting discontinuities or errors in the patterns on the substrate and generating a repair pattern to correct the detected errors.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

The invention claimed is:

1. A method of adaptively generating a pattern for fabricating devices on a surface, the method comprising:
for each layer of a plurality of layers of the devices, as a current layer:
in an offline stage, prior to fabricating the current layer of the devices on the surface, modifying a pattern of the current layer to align with a pattern of any prior layer of the devices previously fabricated on the surface and to account for any previously identified defects on the surface;
in a realtime stage:
obtaining image data of the surface;
identifying defects on the surface from the image data;
dynamically modifying the pattern of the current layer to account for the identified defects that were not previously identified; and
fabricating the current layer of the devices on the surface according to the pattern of the current layer as has been modified in the offline stage and as has further been dynamically modified in the realtime stage.

2. The method of claim 1 wherein fabricating the current layer of the devices on the surface comprises direct-writing the current layer according to the pattern of the current layer as has been modified in the offline stage and as has further been dynamically modified in the realtime stage.

3. The method of claim 1, wherein the devices comprise at least one of: a semiconductor device; a passive electronic device; a logic block; a MEMS device; a photonic device; and a fluidic device.

4. The method of claim 1, wherein obtaining image data of the surface comprises capturing image data of the surface using an imaging system.

5. The method of claim 4, wherein the imaging system comprises an imaging laser scanning the surface at an infra-red wavelength.

6. The method of claim 1, wherein the surface comprises a surface of a polymer film.

7. A system for adaptively generating a pattern for fabricating devices on a surface, the system comprising:
an imaging system for obtaining image data of the surface; and
a processor to:
for each layer of a plurality of layers of the devices, as a current layer:
in an offline stage, prior to fabricating the current layer of the devices on the surface, modify a pattern of the current layer to align with a pattern of any prior layer of the devices previously fabricated on the surface and to account for any previously identified defects on the surface;
in a realtime stage:
obtain image data of the surface;
identify defects on the surface from the image data;
dynamically modify the pattern of the current layer to account for the identified defects that were not previously identified; and
fabricate the current layer of the devices on the surface according to the pattern of the current layer as has been modified in the offline stage and as has further been dynamically modified in the realtime stage.

8. The system of claim 7, wherein the system is configured to operate at a rate between 1 and 7 Gpixels/s.

9. The system of claim 7, wherein the imaging system comprises an imaging laser configured to scan the surface at an infra-red wavelength.

10. The system of claim 7, wherein the surface comprises a surface of a polymer film.

* * * * *